(12) United States Patent
Greenburg

(10) Patent No.: US 10,383,758 B1
(45) Date of Patent: Aug. 20, 2019

(54) DENTAL APPLIANCE

(76) Inventor: Laura Greenburg, Calabasas, CA (US)

( * ) Notice: Subject to any disclaimer, the term of this patent is extended or adjusted under 35 U.S.C. 154(b) by 0 days.

(21) Appl. No.: 13/068,664

(22) Filed: May 17, 2011

Related U.S. Application Data

(60) Provisional application No. 61/395,829, filed on May 17, 2010.

(51) Int. Cl.
*A61F 5/56* (2006.01)

(52) U.S. Cl.
CPC .................................. *A61F 5/566* (2013.01)

(58) Field of Classification Search
CPC .......... A61F 5/0006; A61F 5/56; A61F 5/566; A61C 7/08; A63B 71/08
USPC ..... 128/846, 848, 859–862; 602/902; 433/6, 433/140
See application file for complete search history.

(56) References Cited

U.S. PATENT DOCUMENTS

| | | | |
|---|---|---|---|
| 3,207,153 A * | 9/1965 | Goldstein ...................... | 128/862 |
| 5,607,300 A * | 3/1997 | Tepper .............................. | 433/6 |
| 5,823,193 A * | 10/1998 | Singer et al. .................. | 128/848 |
| 6,178,967 B1 * | 1/2001 | Barnes, Sr. .................... | 128/859 |
| 6,467,484 B1 * | 10/2002 | De Voss ......................... | 128/848 |
| 6,716,029 B2 * | 4/2004 | Fischer et al. ................ | 433/140 |
| 6,766,802 B1 * | 7/2004 | Keropian ....................... | 128/848 |
| 7,156,654 B2 * | 1/2007 | Inman ................................ | 433/7 |
| 7,159,591 B2 * | 1/2007 | Kussick ......................... | 128/848 |
| 7,451,767 B2 * | 11/2008 | Keropian ....................... | 128/848 |
| 7,861,724 B2 * | 1/2011 | Keropian ....................... | 128/848 |
| 8,132,567 B2 * | 3/2012 | Keropian ....................... | 128/848 |
| 8,333,202 B2 * | 12/2012 | Lyons ............................ | 128/848 |
| 2005/0011525 A1 * | 1/2005 | Goyette ......................... | 128/861 |
| 2008/0000483 A1 * | 1/2008 | Halstrom ....................... | 128/848 |
| 2009/0056724 A1 * | 3/2009 | Keropian ....................... | 128/848 |
| 2009/0120448 A1 * | 5/2009 | Keropian ....................... | 128/848 |
| 2009/0241969 A1 * | 10/2009 | Walker .......................... | 128/848 |
| 2011/0017220 A1 * | 1/2011 | Lindsay et al. ............... | 128/848 |
| 2011/0120476 A1 * | 5/2011 | Keropian ....................... | 128/848 |
| 2011/0226264 A1 * | 9/2011 | Friedman et al. ............. | 128/848 |
| 2011/0297162 A1 * | 12/2011 | Navarro Segura et al. .. | 128/848 |

\* cited by examiner

*Primary Examiner* — Tarla R Patel
(74) *Attorney, Agent, or Firm* — Steven E. Shapiro

(57) ABSTRACT

The invention is a dental appliance to open the airway for individuals who suffer with snoring or sleep apnea. The appliance includes a base which will fit over the lower teeth, the upper teeth or both. It can be custom made or generic to fit many people. A key component includes a tongue restraining device. The tongue restraining device is a flexible, moveable transverse band that deforms during tongue movement such as swallowing, allowing a degree of comfort to the tongue during that movement and then because of the memory of the band, returns the tongue to its original position. A mechanism will usually be included that advances the mandible. This can be done in many ways. The tongue restraining device can be added to any existing dental appliance. Even appliances that are not for the purpose of treating snoring and/or sleep apnea.

7 Claims, 6 Drawing Sheets

DENTAL APPLIANCE

CROSS-REFERENCE TO RELATED APPLICATIONS

The applicant hereby claims benefit of U.S. Provisional Patent Application No. 61/395,829 (filed May 17, 2010). The specification of said provisional patent application is incorporated herein by this reference as though set forth in full.

STATEMENT REGARDING FEDERALLY SPONSORED RESEARCH OR DEVELOPMENT

Not Applicable

FIELD OF INVENTION

The present invention relates to dental appliances for the treatment of snoring and sleep apnea.

BACKGROUND OF THE INVENTION

Medical studies have shown that snoring can have serious medical consequences for people. Many people who snore suffer from Obstructive Sleep Apnea. If not diagnosed or if left untreated, Obstructive Sleep Apnea can result in severe medical consequences such as systemic high blood pressure, cardiovascular disease, stroke and heart attack.

Spouses also suffer through the night from the noise of the snorer and their stoppage of breathing. Snoring and sleep apnea not only disturbs the sleeping pattern of the snorer, it is also disruptive to his or her spouse. This leaves both unrefreshed, tired and sleepy throughout the day. It can cause sleepiness while driving, reading, working or doing other tasks.

A broad variety of intra-oral and dental appliances and devices are now available to treat a patient for snoring and sleep apnea. However, most of these are uncomfortable to the user and studies have shown that the vast majority of these devices go unused. Other treatments for snoring and sleep apnea include various surgeries, which are drastic steps that can have significant adverse consequences to the patient and often do not work in any event.

The present invention is a dental oral appliance for use with patients who suffer with sleep disorders, to reduce or eliminate snoring and to open the airway for a sleeping individual who suffers with sleep apnea.

SUMMARY OF THE INVENTION

The present invention is a dental oral appliance, for use with patients who suffer with sleep disorders, to reduce or eliminate snoring and to open the airway for a sleeping individual who suffers with sleep apnea. The appliance also opens the airway in an awake individual, whose tongue partially blocks/obstructs the airway thereby increasing the airflow in and out and allows more relaxed fuller breathing. This is accomplished as the tongue is trained by the patient wearing the appliance at night to re-position itself forward and up. The appliance can cover just the lower teeth, just the upper teeth or both the lower and upper teeth. It has an open center where the tongue sits. The portion of the appliance that covers the teeth can be custom fit for the specific patient or of a more generic type where one size fits many patients. The appliance can fit snuggly or loosely on the teeth to secure the appliance within the mouth. The appliance works whether the mouth is able to open or if it is designed to keep it closed.

There is a flexible, moveable transverse band that extends from the lower right molars to the lower left molars that pushes the tongue upward and forward, thereby breach the airway. In the past, appliances that addressed the tongue were very uncomfortable because they prevented the tongue from being able to move back to swallow. The flexible, moveable transverse band allows the tongue significant freedom to swallow. The act of the tongue moving backward to swallow stretches the elastic type band. Once the swallowing motion is complete, the tongue relaxes allowing the transverse band to re-coil to its original un-stretched position, thereby bringing the tongue back forward and re-opening the airway. This allows much greater comfort and therefore increased compliance and use by the individual. The flexible, moveable transverse band can be any shape and made out of any material that allows it to change position, allowing greater comfort for the tongue's movements and then rebounds to its original position bringing the tongue to a position whereby the airway opening is increased.

The dental appliance can comprise a single piece of material. However, in most cases the mouth piece (the portion engaging the teeth) and the tongue restraining device will be separate pieces. The reason for this design is that the size of everyone's mouth and tongue is different. Therefore the position of the flexible, moveable transverse band in terms of anterior-posterior, as well as angulation in a vertical plane, needs to have the ability to move to fit each person. By having the flexible, moveable transverse band as a separate member, it can be attached with simple buttons or any other type of fastening methods known to those of skill in the art.

Over time, as the tongue is trained to stay in position during sleep, the device can be adjusted to increase forward positioning of the tongue. After the tongue is fully trained to stay in position, some patients will no longer need to wear the device on a daily basis to avoid snoring and/or sleep apnea. The flexible, moveable transverse band can be designed to be a permanent part of the appliance or removable so it can be replaced, modified or taken off depending upon the needs and circumstances.

The appliance can be modified so it can be used by people missing some teeth, many teeth or even all their teeth by containing the flexible, moveable transverse band within a lower appliance, an upper appliance or appliance fitting over both the upper and lower teeth and/or dentures.

The flexible, moveable transverse band can be added to any existing dental appliance used for the treatment of snoring and/or sleep apnea to increase their effectiveness. It can also be used for dental appliances/prosthesis that are not for the purpose of treating snoring and/or sleep apnea. Some of these types of appliances include but are not limited to orthodontic retainers, orthodontic appliances, athletic enhancement appliances, bleaching trays, night-guards, bruxism appliances, fluoride trays, partial dentures, full dentures and implants.

BRIEF DESCRIPTION OF THE DRAWINGS

The above and other objects and advantages of the present invention will be apparent upon consideration of the following detailed description, taken in conjunction with the accompanying drawings, in which reference characters refer to like parts throughout, and in which.

DETAILED DESCRIPTION OF THE INVENTION

Figure 1:
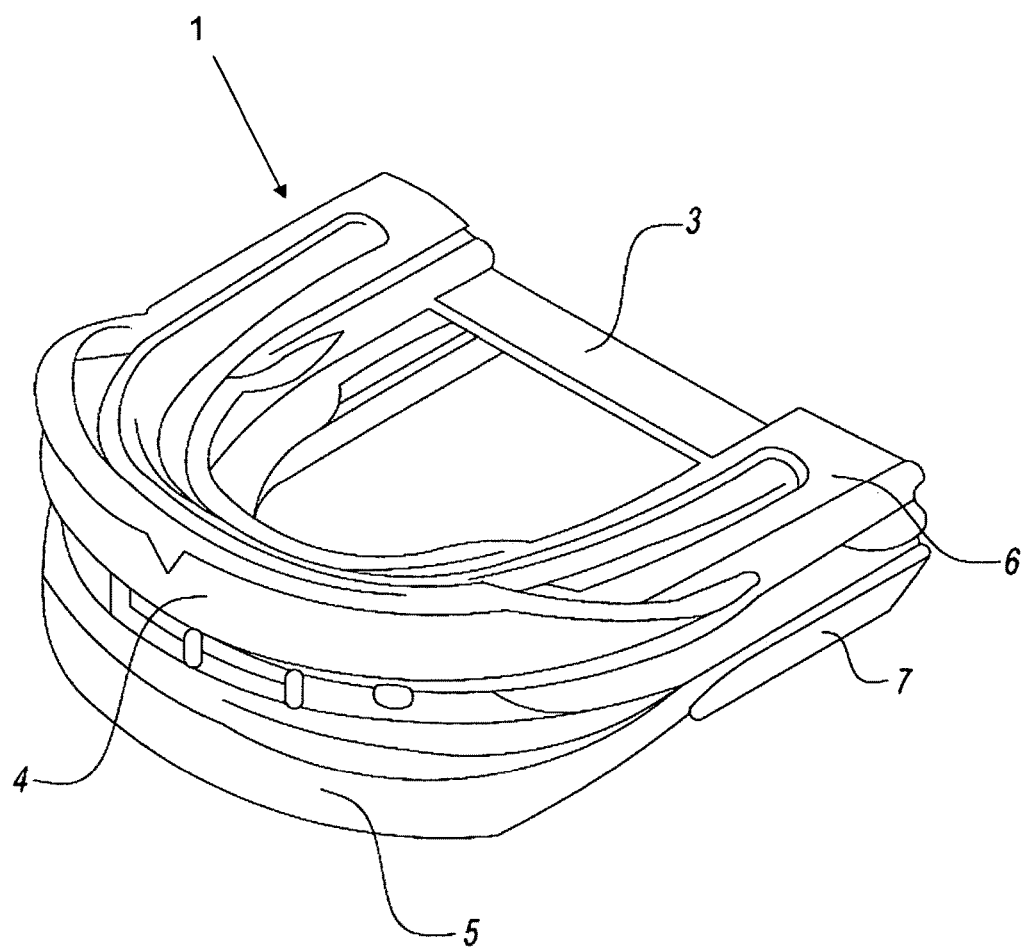
FIG. 1 illustrates one embodiment of an appliance utilizing the flexible, moveable transverse band.

FIG. 1 illustrates an example of an appliance 1 utilizing the flexible, moveable transverse band 3. The transverse band can be made out of rubber, silicone or similar material that can be moved by the tongue and then rebound to its original position. It has an upper section 4 and lower section 5 that the user bites into. The upper section 4 and lower section 5 can be acrylic shells and are typically rigid. The upper section 4 is filled with an upper piece 6 of rubbery, moldable material that becomes very soft and moldable when heated in hot water. Similarly, lower section 5 is filled with a lower piece 7 of rubbery, moldable material that becomes very soft and moldable when heated in hot water. The user bites into the moldable material (6 and 7) when the material is in a heated, soft and moldable state and stays biting while the material cools. As the material cools, it hardens, retaining the new shape and thereby securing both the upper and lower teeth in the appliance. Other materials can be used as are known to those with skill in the art. Other types of appliances can be utilized in the invention utilizing the flexible, moveable transverse band 3. For example, the base might secure to the upper teeth only or the lower teeth only. The flexible, moveable transverse band 3; can also be secured to other existing appliances for the treatment of snoring and sleep apnea to improve the success and results of those other appliances. It is preferred that the flexible, moveable transverse band 3 is placed as far posterior as possible for maximum effectiveness.

Figure 2:
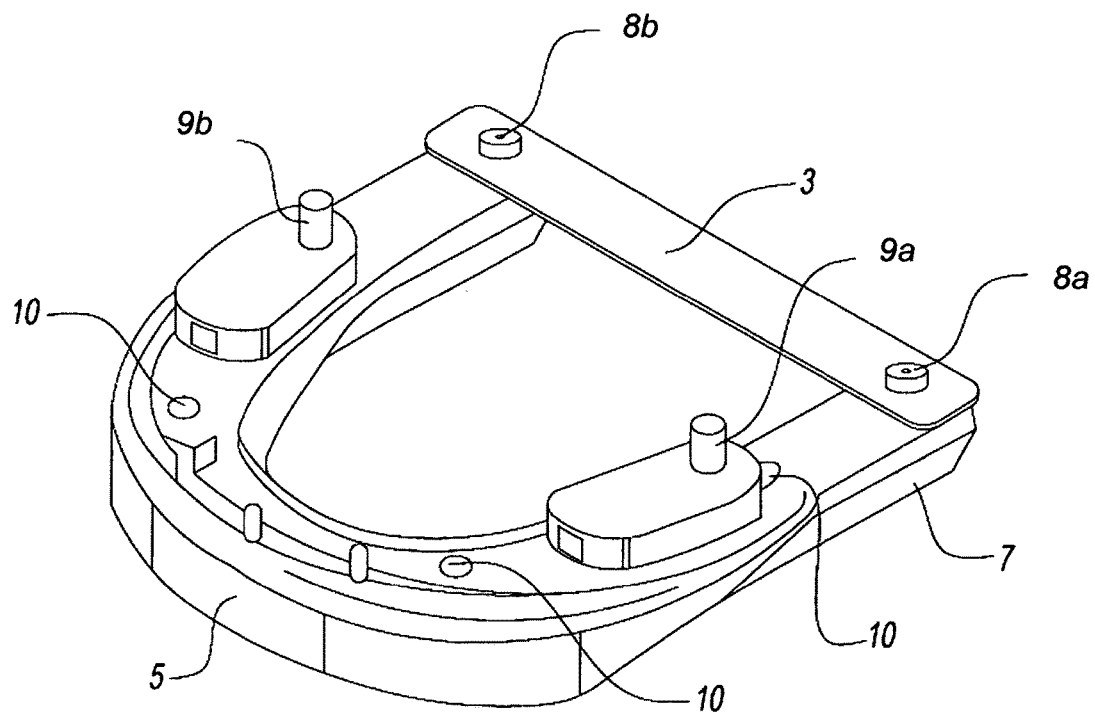
FIG. 2 shows the securing means of the flexible, moveable transverse band on the bottom portion of the appliance.

FIG. 2 shows the lower section 5 of the device depicted in FIG. 1 (without the top, upper portion). The lower section has a left, back post 8a and a right, back post 8b. The flexible, moveable transverse band 3 fits over these two posts so that it can stays in place. As can be seen in FIG. 2, the tongue restraining device (the flexible moveable transverse band) 3 extends from the ends of the lower section 5. When the dental appliance is positioned in the patient's mouth, the tongue restraining device keeps the tongue from falling back, thereby keeping it from blocking the airway. This keeps the airway open and prevents/reduces the number of apneic events (the number of times the tongue falls back and blocks the airway for at least 10 seconds). Left, middle post 9a and right, middle post 9b are positioned on the surface of the lower section. These posts snap into holes on the upper section to keep the upper and lower sections together. The base also has a hole 10 formed therein that allow the lower piece of rubbery, moldable material 7 to go through to lock into the lower section 5. It is also possible to form the lower section 5 as a custom lab fabricated piece, molded specifically to the user's teeth without the need for the lower piece of rubbery, moldable material 7.

Figure 3:
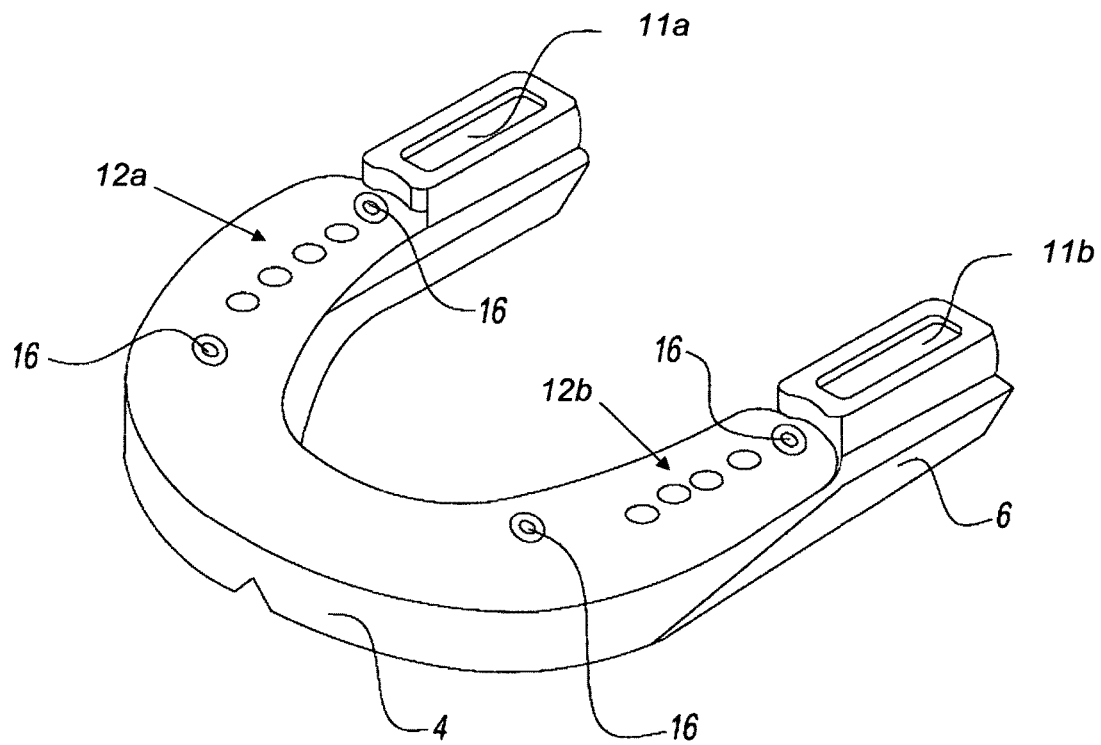
FIG. 3 shows the top portion of the appliance.

FIG. 3 shows the upper section 4 of the appliance in FIG. 1 upside down, so that the bottom surface of the upper section 4 can be seen. The upper piece of rubbery, moldable material 6 has a left groove 11a and a right groove 11b. When the device is assembled, the left groove 11a accepts the left post 8a and the right groove 11b accepts the right post 8b to lock the flexible moveable transverse band 3 into place. The bottom surface of the upper section 4 has a left row of holes 12a formed in the surface of the left side and a right row of holes 12b formed on the right side. When the device is assembled, the left row of holes 12a accepts the left post 9a and the right row of holes 12b accepts the right post 9b to further secure the upper section 4 and lower section 5 together. The posts 9a and 9b can be placed in the holes according to the amount desired to move the jaw of the user forward. Placing the posts in the holes closest to the front will maximize the amount of movement forward by the jaw and placing the posts in the holes farthest from the front will minimize the amount of movement forward by the jaw. This helps to alleviate snoring and sleep apnea. The hole 16 allows the upper piece of rubbery moldable material 6 to go through to lock into the upper section 4. It is also possible to form the upper section 4 as a custom lab fabricated piece, molded specifically to the user's teeth without the need for upper moldable material piece 6.

Figure 4:
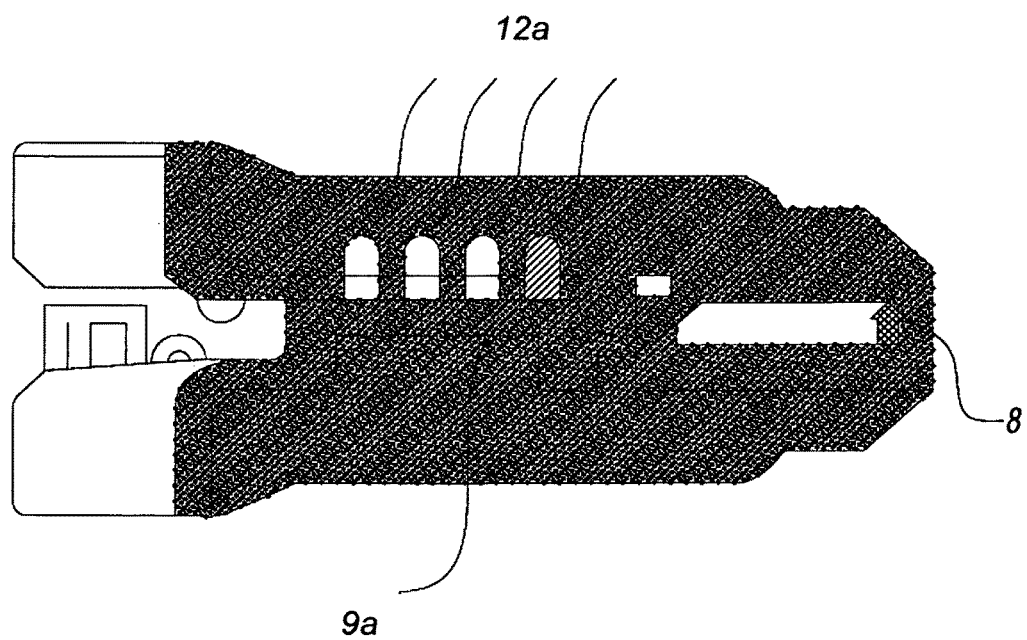
FIG. 4 shows a sectioned view of the dental appliance viewed from the side.

FIG. 4 shows a sectioned view of the dental appliance in FIG. 1 as viewed from the side. In this view, the post 9a, is in one of the row of holes 12a. In this position, the mandible, lower jaw is in its most posterior, retruded position. By placing the left post 9a in the hole of row of holes 12a that is farthest from the front. It could be placed in one of the other holes to move the mandible forward. The more forward the mandible is positioned, the more the tongue is brought forward and the more the airway is opened, thereby reducing both snoring and apneic events that define sleep apnea. The left post 8a is the post that the flexible, moveable transverse band 3 is attached to so that the band 3 can keep the tongue from falling back, thereby reducing snoring and sleep apnea.

Figure 5:
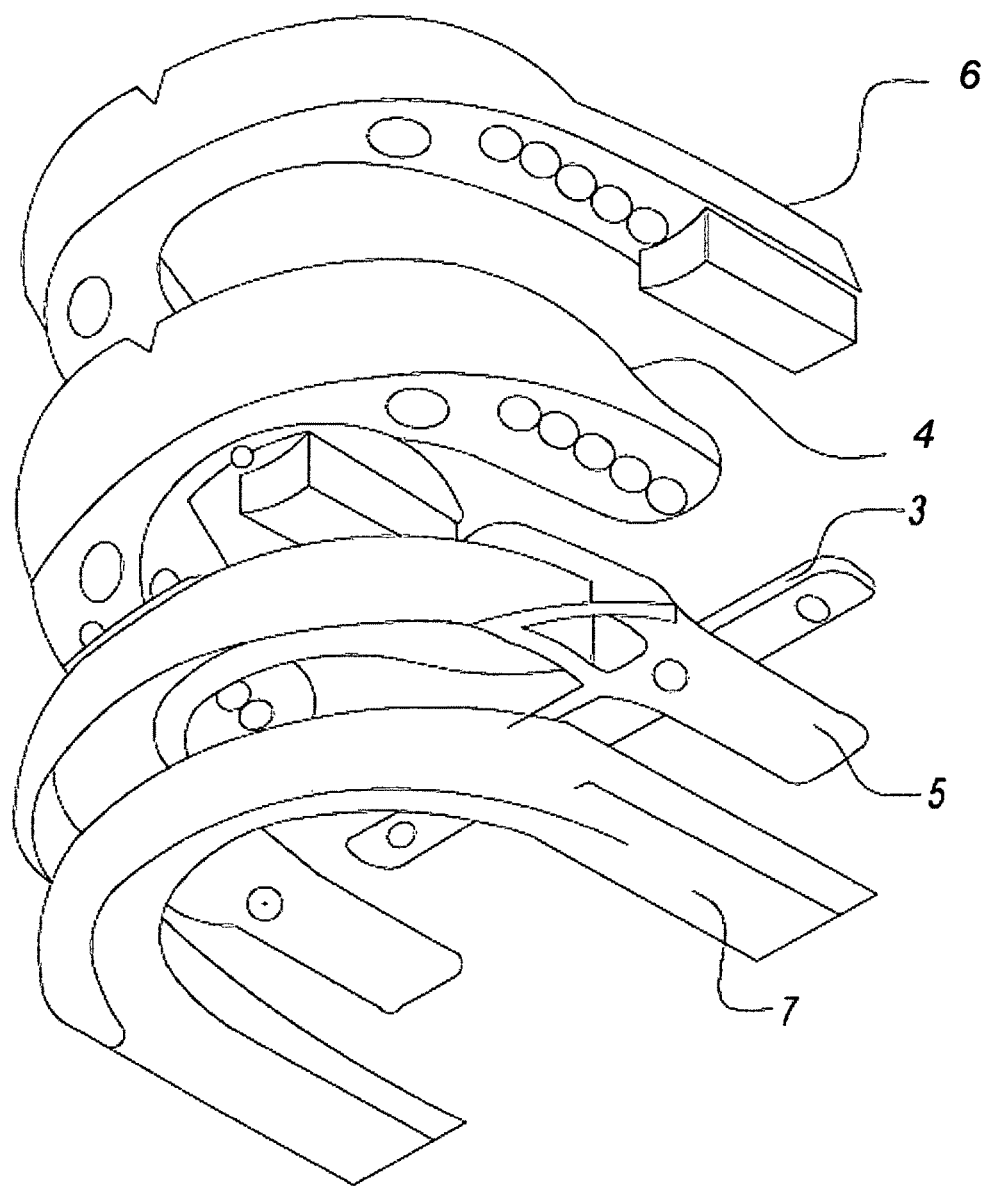
FIG. 5 provides an exploded view of four pieces comprising the embodiment of the dental appliance plus the flexible, moveable transverse band from below, looking up.

FIG. 5 shows the four pieces of the dental appliance plus the flexible, moveable transverse band 3, from below, looking up.

Figure 6:
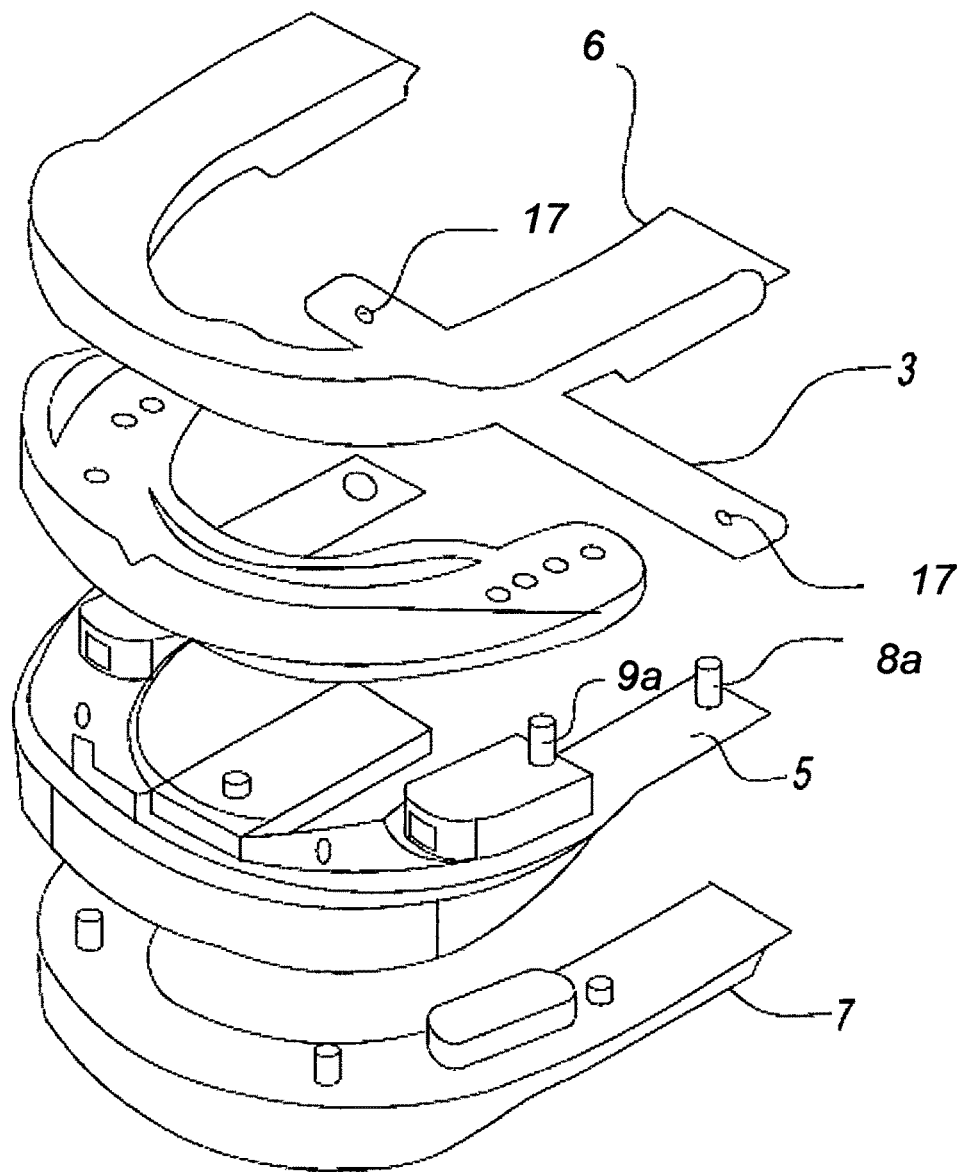
FIG. 6 provides an exploded view of four pieces comprising the embodiment of the dental appliance plus the flexible, moveable transverse band from above, looking down.

FIG. 6 shows the four pieces of the dental appliance plus the flexible, moveable transverse band, 3 from above, looking down.

The tongue restraining device, the flexible, moveable transverse band, 3 is positioned such that when the tongue goes up and back to swallow, the tongue comes in contact with the band 3. As the swallowing motion continues, the band deforms, moving to allow the tongue to continue its desired swallowing motion. Once the tongue has completed its swallowing motion and relaxes, the memory from the band brings the tongue back forward and out of the airway. By only allowing the tongue to go back into the airway temporarily and for short periods of time, both snoring and sleep apnea are substantially reduced. Material from the band can be made of silicone, rubber, elastic or any other material that allows itself to become deformed but retains its memory and goes back to its original shape after the pressure causing the deformation is stopped. The band 3 is connected to the lower section 5, by having holes 17 in it. The holes 17 slide over the posts (8a and 8b) on the lower section 5. When the upper section 4 and upper piece of rubbery, moldable material 6 are placed on top of the lower section 5 and lower piece of rubbery, moldable material 7 which snap together, the band; 3 is locked into place and cannot be removed.

It is possible for the lower section 5 and lower piece of rubbery, moldable material 7 to be formed as one unit and the upper section 4 and upper rubbery, moldable material 6 to be formed as one unit, comprising 2 units, both an upper and a lower. To do this would involve taking impressions of both the upper and lower teeth and then fabricating the pieces out of acrylic or other plastic. Some appliances can be made by further reducing the 2 pieces, upper and lower to just 1 whereby the upper and lower are permanently joined in the manufacture of the appliance. Materials that are commonly used to make moldable mouth guards can be used for this purpose to manufacture any of these appliances.

In one embodiment, the lower section 5 and the tongue restraining device 3 are connected by an adjustable connection means such as a ratchet mechanism that allows the position of the tongue restraining device 3 to be adjusted. It is preferred that the adjustable connection means allows the tongue restraining device 3 to be lengthened and/or raised/lowered pivotally with respect to the lower section 5. By having the "tongue restraining device" as a separate member, it can be attached with a ratchet-type hinge for vertical angulation as well as a sliding-slot mechanism for the anterior-posterior adjustment.

Various types of adjustment means known to those skilled in the art can be utilized to allow length and/or pivotal adjustment of the tongue restraining device. Examples of such adjustment means are described in the following US Patents: U.S. Pat. No. 7,415,912 (adjustable components (300 and 400 shown on in the figure on the front page) can be lengthened and shortened with locking screws in slots); U.S. Pat. No. 7,399,288 (adjusting rod to lengthen and shorten neck brace); U.S. Pat. No. 7,384,406 (adjustable-length strut); U.S. Pat. No. 7,377,779 (means to adjust posts); U.S. Pat. No. 7,320,672 (means to adjust angular extension); U.S. Pat. No. 7,166,132 (means to pivotally adjust bone prosthesis); U.S. Pat. No. 7,156,654 (means to lengthen orthodontic appliance); U.S. Pat. No. 7,037,287 (adjustable pivot mechanism for knee brace (see FIG. 6)); U.S. Pat. No. 6,964,566 (adjustment means for lengthening dental oral appliance (see FIG. 9)); U.S. Pat. No. 6,960,175 (adjustment means for pivot in leg brace (see FIGS. 2 and 3)); U.S. Pat. No. 6,926,363 (mechanism for adjusting angle of hinge); U.S. Pat. No. 6,796,951 (mechanism for pivotal adjustment (see FIG. 6)); U.S. Pat. No. 6,783,361 (length in dental appliance adjusted by jack screw controlled by a ratchet); U.S. Pat. No. 6,739,277 (length adjustment mechanism (see FIG. 2)); U.S. Pat. No. 6,656,144 (mechanism for pivotal joint); U.S. Pat. No. 6,629,841 (pivot adjustment mechanism (see FIG. 5)); U.S. Pat. No. 6,523,492 (length adjustment mechanism); U.S. Pat. No. 6,413,232 (pivot adjustment member (see FIGS. 4 and 5); and U.S. Pat. No. 6,383,156 (range of motion hinge with an adjustable length strut (see FIGS. 2A through 8). The complete specification of each patent listed in the previous sentence is incorporated herein by this reference as though set forth in full.

In the some of the practices, the tongue restraining device will be lengthened and pivoted downward as the tongue is trained to stay in good position. This can be accomplished in a number of ways, as discussed above. For example, a plurality of appliances can be manufactured at one time for the patient (typically, three to seven). The base will be the same for each appliance (specially molded according to the lower teeth of the patient). However, the tongue restraining device, which includes the flexible, moveable transverse band as well as the attachment of the band to the appliance, will get progressively longer with a more downward slope. The first appliance will have a relatively short tongue restraining device that slopes slightly downward from the base connection points. After the patient has gotten use to the new appliance and the tongue is partially trained, the practitioner can then give the patient the second appliance. The tongue restraining device on the second appliance will be somewhat longer and will have a more downward slope from the base connection points. This process will continue until the tongue restraining device keeps the tongue in a completely correct posture.

The same type process can be accomplished by fabricating new appliances as they are needed. Also, an adjustable appliance, as described above, can be used for this purpose. The number of adjustments required will vary depending on the patient's ability to tolerate the appliance and the changes. Typically, the number of adjustments will be from three to seven. However, 10 or more adjustments might be required.

FIG. 6 provides a version of the dental appliance viewed from above (top view). The purpose of here is to permit discussion of the possible dimensions of the appliance's components. In the example shown in FIG. 6, the length of the flexible, moveable transverse band 3 is about 6 centimeters. This length is due directly to the width of the last left molar of the patient.

Various sizes are possible. This width depends on the size of the lower jaw. In one possible embodiment, the dimensions of the band might be about 6 cm long by 1 cm wide by 1 mm thick and made out of rubber that is latex free and antimicrobial. In this version, the tongue might displace the center of the elastic band anywhere from one to 2.5 cm during swallowing. The length of the band will be determined by the width of the mandible and in most cases approximating where the lower $2^{nd}$ molar is positioned. There are other instances where the band can be narrower and only about 0.5 cm in width. This allows greater displacement of up to 3 cm with less force by the tongue. A silicone elastic band can provide similar elasticity and displacement to the rubber.

In FIG. 4, the length of the left row of holes 12a is approximately 12 mm or 3 mm between each hole. The same is true of the right row of holes 12b. This allows the lower jaw, mandible, to be advanced 3 mm from each position or a total of 12 mm between its most rearward position and its most advanced, forward position. Depending upon the size of the jaw and the population the appliance is being used for, these distances can be larger or smaller.

There is no exact way to determine the optimal length of a flexible, moveable transverse band. The length will be determined by the width between the last molar on the lower left side and the last molar on the lower right side.

It should be noted that shapes other than a straight flexible, moveable transverse band are possible for the tongue restraining device. It could be shaped as a "U" going posteriorly or anteriorly as well as a "U" going superiorly or inferiorly. The tension on the flexible, moveable transverse band can be neutral; not exerting any pressure, varying degrees of tightness or with significant looseness or slack.

The invention claimed is:

1. A dental oral appliance to open the airway for a sleeping individual who suffers with snoring or sleep apnea comprising: a base comprising a first section configured to accept a first group of teeth of the individual and a right posterior end and a left posterior end; and a tongue restraining device connected to the base at said right posterior end and at said left posterior end, said tongue restraining device consisting only of a flexible, moveable transverse band, wherein the base comprises an upper section and a lower section and the relative position of the upper section to the lower section can be adjusted.

2. A dental oral appliance to open the airway for a sleeping individual who suffers with snoring or sleep apnea comprising: a base comprising a first section configured to accept a first group of teeth of the individual and a right posterior end and a left posterior end; and a tongue restraining device connected to the base at said right posterior end and at said left posterior end, said tongue restraining device consisting only of a flexible, moveable transverse band, wherein the flexible, moveable transverse band is straight across from said right posterior end to said left posterior end, when it is not deformed by the individual's tongue.

3. The appliance of claim 2, wherein said flexible, moveable transverse band is substantially rectangular in shape, having a length, width and thickness.

4. The appliance of claim 3, wherein said thickness is about 1 millimeter.

5. The appliance of claim 4, wherein said length is about 1 centimeter wide.

6. The appliance of claim 4, wherein said width is about 0.5 centimeters-wide.

7. The appliance of claim 3, wherein said flexible, movable transverse band is positioned such that when the tongue goes up and back to swallow, the tongue comes into contact with the band.

* * * * *